United States Patent
Kurz et al.

(10) Patent No.: US 6,892,466 B2
(45) Date of Patent: May 17, 2005

(54) DEVICE FOR DETERMINING A LENGTH OF A MIDDLE EAR PROSTHESIS

(75) Inventors: Heinz Kurz, Dusslingen (DE); Uwe Steinhardt, Hirrlingen (DE)

(73) Assignee: Heinz Kurz GmbH Medizintechnik, Dusslingen (DE)

( * ) Notice: Subject to any disclaimer, the term of this patent is extended or adjusted under 35 U.S.C. 154(b) by 0 days.

(21) Appl. No.: 10/782,204

(22) Filed: Feb. 19, 2004

(65) Prior Publication Data

US 2004/0167624 A1 Aug. 26, 2004

(30) Foreign Application Priority Data

Feb. 21, 2003 (DE) .................................... 203 02 850 U

(51) Int. Cl.⁷ .......................... G01B 5/02; A61B 5/103; A01F 2/18
(52) U.S. Cl. .............................. 33/512; 33/562; 623/10; 600/587
(58) Field of Search ......................... 33/511, 512, 562; 600/587; 623/10

(56) References Cited

U.S. PATENT DOCUMENTS

| | | | | |
|---|---|---|---|---|
| 466,044 A | * | 12/1891 | Jacobs .......................... | 33/562 |
| 1,881,651 A | * | 10/1932 | Judge ........................... | 33/562 |
| 3,238,629 A | * | 3/1966 | Hurwitz ........................ | 33/562 |
| 4,362,681 A | * | 12/1982 | Spector et al. ................ | 264/112 |
| 4,517,747 A | * | 5/1985 | Morin .......................... | 33/512 |
| 4,921,498 A | * | 5/1990 | Bays et al. .................... | 623/10 |
| 5,554,188 A | * | 9/1996 | Prescott ....................... | 623/10 |
| 5,618,292 A | * | 4/1997 | Poler ........................... | 33/512 |
| 5,814,098 A | * | 9/1998 | Hinnenkamp et al. ....... | 600/587 |
| 6,168,625 B1 | * | 1/2001 | Prescott ....................... | 623/10 |
| 6,637,121 B2 | * | 10/2003 | Barefoot ....................... | 33/562 |
| 6,726,719 B2 | * | 4/2004 | Antonelli et al. ............. | 623/10 |
| 2003/0069613 A1 | * | 4/2003 | Kuzma et al. ................ | 607/40 |
| 2004/0181280 A1 | * | 9/2004 | Antonelli et al. ............. | 623/10 |

* cited by examiner

Primary Examiner—G. Bradley Bennett
(74) Attorney, Agent, or Firm—Michael J. Striker

(57) ABSTRACT

A device for determining a length of a middle ear prosthesis has a base part for mounting prosthesis models of different lengths, and an applicator with which the prosthesis models after being released from the base part, are introducible during an operation into the middle ear.

12 Claims, 2 Drawing Sheets

DEVICE FOR DETERMINING A LENGTH OF A MIDDLE EAR PROSTHESIS

BACKGROUND OF THE INVENTION

The present invention relates to a device for determining a length of a middle ear prosthesis.

In order to transmit the sound from an eardrum to a rising bracket or to a rising bracket foot plate in the case of completely or partially defective auditory ossicles, ossicles prostheses are utilized. Since the anatomic properties of ear of different human beings are different to a certain degree, it is necessary to use auditory ossicles prosthesis whose dimensions are adjusted to specific properties of the ear in which it must be utilized. In particular, the distance between the eardrum and the rising bracket footplate in the case of a total reconstruction or the distance between the eardrum and the rising bracket body in the case of a partial reconstruction must be determined.

Conventionally, for this purposes prosthesis mounts with different sizes, in particular with different lengths composed of high grade steel are utilized. The prosthesis mounts are introduced during the operation in the middle ear, until the prosthesis models determining the sizes are found. After the determination of the sizes, the prosthesis models as a rule are again sterilized by steam sterilization in the clinic and are again available for a new size determination.

The prosthesis models are naturally small. The sterilization is therefore very difficult to handle. In order to obtain a sufficient sterilization, preliminarily an exactly defined cleaning process must be carried out. Since the prosthesis mounts are so small, there is a risk that they can be lost during the sterilization or in the course of cleaning. Since the prosthesis mounts are produced of metal, in particular high grade metal, so that they are capable of being sterilized and have a sufficient strength, they are very heavy. This means that they can be tilted during their investigated placement in the middle ear, so that a correct determination of the size of the adjusted prosthesis requires significant skills.

SUMMARY OF THE INVENTION

Accordingly, it is an object of the present invention to provide a method of determination of a length of a middle ear prosthesis, which eliminates the disadvantages of the prior art.

More particularly, it is an object of the present invention to provide a device for determination of a length of a middle ear prosthesis, with which the prosthesis models may be available in an easy-to-handle manner and do not require any sterilization.

In keeping with these objects and with others which will become apparent hereinafter, one feature of the present invention resides, briefly stated, in a device which has a base part for mounting prosthesis models of different lengths; and an applicator with which the prosthesis models after being released from said base part, are introducible during an operation into the middle ear.

In the inventive device, for determination of a length of a middle ear prosthesis, differently sized prosthesis models are mounted on the base part. With this arrangement they are presented to a doctor in a way so that he can easily observe them and they can not be lost. The device includes further an applicator, with which the prosthesis models during the operation can be inserted in a middle ear in a reliable manner for determination of the length of the adjusted middle ear prosthesis.

The base part on which the prosthesis models are mounted, can have different shapes and sizes. Round, multi-cornered and tree or bar-shaped designs can be advantageously utilized in the praxis. The size of the base type is selected in accordance with a number of the prosthesis models and their mounting process. In the praxis, a size of 2.5 cm is recommended.

The base part can be composed of the different materials. Plastics are recommended as a sterile and light and inexpensive material for the base part, which can be produced for example by injection molding.

The prosthesis models are secured on the base part by thin webs. These webs can be easily broken by hand with the use of for example a tweezers, to separate the prosthesis model from the base part and to secure on the applicator.

Also, in the case of the prosthesis models it is advisable when they are produced of a synthetic plastic. In this case they can be produced for example together with the base part in one injection molding process in an easy and cost-economical manner. Synthetic plastics, when compared to metals from which the conventional prosthesis models are produced now, are relatively light materials, so that the prosthesis models will have also smaller weight.

During a research introduction of the prosthesis models in the middle ear it is no longer possible that the prosthesis models tilt, and thereby the determination of the adopted size can be performed in a reliable manner. When the synthetic plastic for the prosthesis models does not provide the required strength, then the prosthesis model can have a core composed of metal for its strengthening, or with a targeted insertion of the metal core a desirable weight extension for improved handling is provided.

The applicator can be composed for example of a bar which on the one hand is provided with a pincer-shaped receiving part for receiving the prosthesis model. It can be composed of various materials, in particular of metal or synthetic plastic. For reliably holding the prosthesis model, it is advantageous when the pincer-shaped receiving part is springy. In this case an advantage is provided, when the inner side of the pincer-shaped receiving part is routed.

The individual parts of the inventive device, in particular the base part with the prosthesis models of different lengths mounted on it, and the applicator are packed in a sterile process and retained sterile so that they do not need a sterilization and are ready for use. After the proper length for the later prosthesis is determined, the prosthesis models are disposed, so that a critical cleaning and sterilization can be dispensed with and thereby a risk of infection transmission is eliminated.

The novel features which are considered as characteristic for the present invention are set forth in particular in the appended claims. the invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
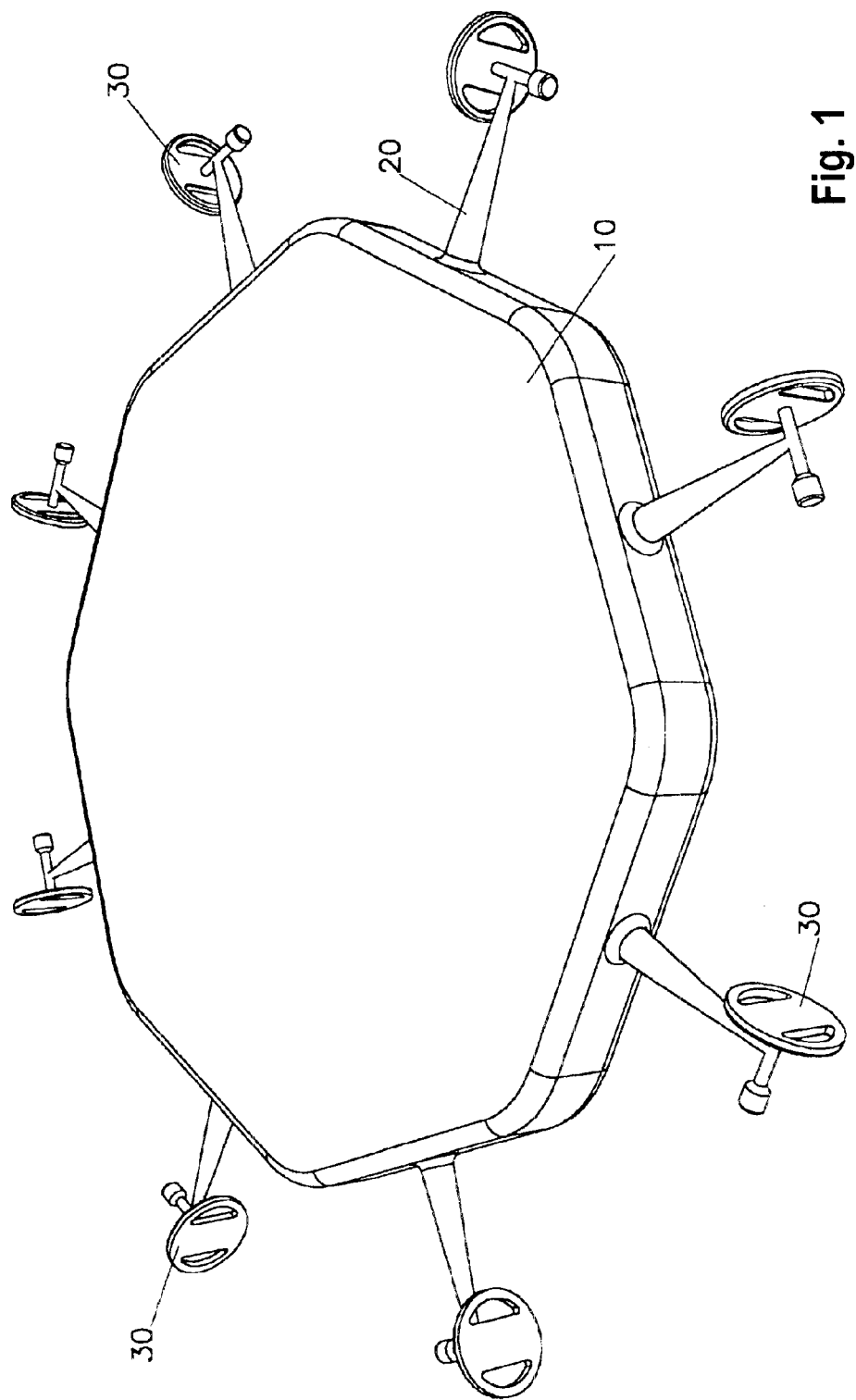
FIG. 1 is a perspective view of one embodiment of a base part of the device for determination of a length of a middle ear prosthesis in accordance with the present invention, with a prosthesis model mounted on it.

A device for determining a length of a middle ear prosthesis has a base part which is shown in a perspective view of FIG. 1. The base part is identified with reference numeral 10. It has the shape of a rounded octagon. A plurality of prosthesis models are mounted on the base part. The prosthesis models are identified with reference numeral 30. Each prosthesis model 30 is secured to the base part through a web 20, in particular to a corresponding side of the octagonal base part, as shown in FIG. 2.

Figure 2:
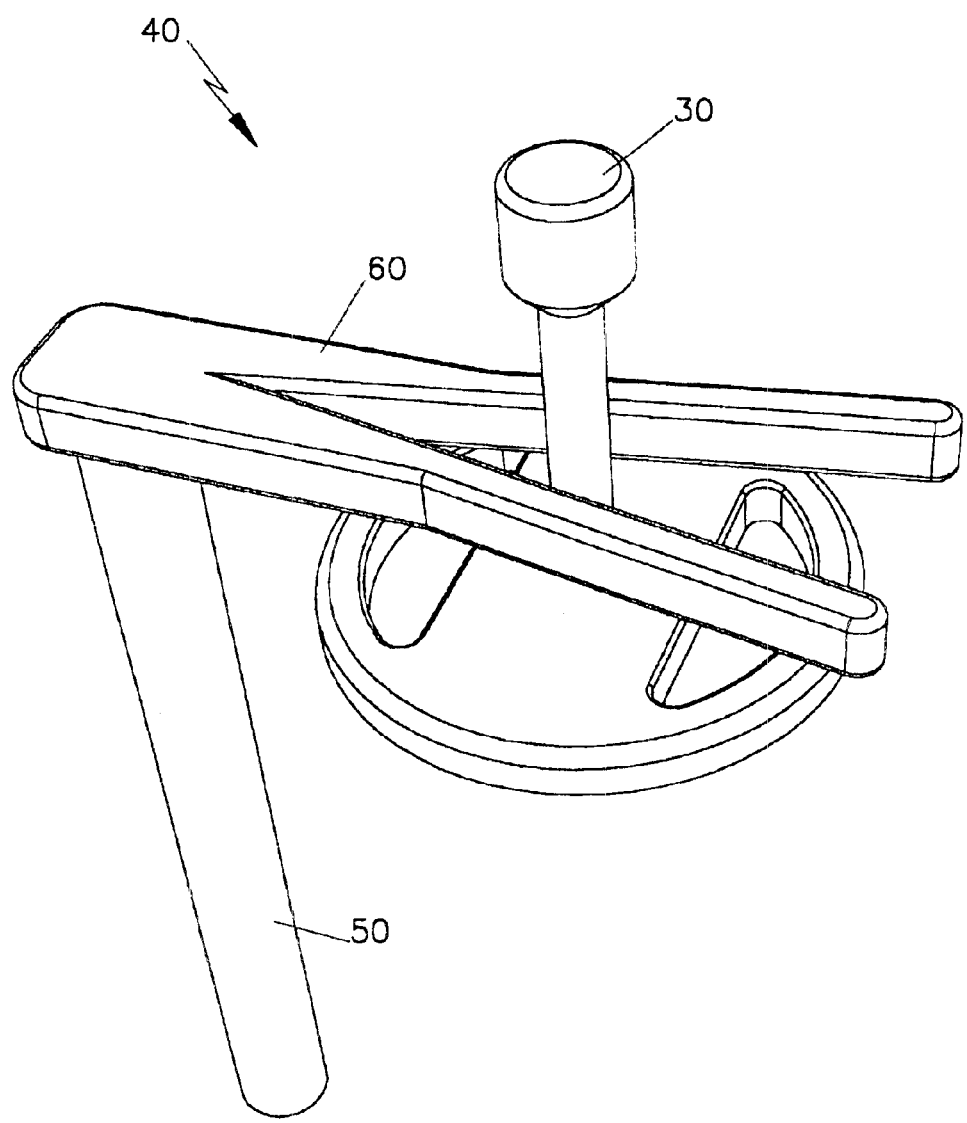
FIG. 2 is a perspective partial view of an embodiment of the applicator of the inventive device with a prosthesis model received in it.

FIG. 2 shows an embodiment of an applicator of the inventive device for determination of a length of a middle ear prosthesis. The applicator is identified as a whole with reference numeral 40. The applicator 40 includes a rod 50 and a pincer-shaped receiving part 60. The prosthesis model 30 is received in the pincer-shaped receiving part 60. Thereby it can be easily introduced with the applicator, for example into the middle ear, for determination of an appropriate size of the later prosthesis.

The base part 10 can have different shapes and sizes, for example it can be round, multi-cornered, tree-shaped or bar-shaped. It can have the size of 3.5 cm. Also, the base part can be composed of various materials, and produced for example by injection molding.

The webs 20, with which the prosthesis models 30 are connected to the base part, can be easily broken by tweezers to separate the prosthesis models from the base part and to secure them on the applicator 40.

The prosthesis models can be composed of synthetic plastic material. Also, they can be produced together with the base part in an injection molding process. Furthermore, the prosthesis models can be reinforced with a metal core.

The applicator can be composed of various materials, for example of metal or synthetic plastic. The pincer-shaped receiving part 60 of the applicator 40 can be springy.

It will be understood that each of the elements described above, or two or more together, may also find a useful application in other types of constructions differing from the types described above.

While the invention has been illustrated and described as embodied in device for determining a length of a middle ear prosthesis, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of the invention.

What is claimed as new and desired to be protected by Letters Patent is set forth in the appended claims:

1. A device for determining a length of a middle ear prosthesis, comprising a base part for mounting prosthesis models of different lengths; and an applicator with which the prosthesis models after being released from said base part, are introducible during an operation into the middle ear.

2. A device as defined in claim 1, wherein the base part has a shape selected from the group consisting of a round shape, a corner shape, a tree-shape, and a bar shape.

3. A device as defined in claim 1, wherein said base part is composed of synthetic plastic.

4. A device as defined in claim 1, wherein said base part has a size substantially corresponding to 2.5 cm.

5. A device as defined in claim 1; and further comprising substantially thin and manually breakable webs which are arranged to connect the prosthesis models with said base part.

6. A device as defined in claim 1, wherein the prosthesis models are composed of a synthetic plastic.

7. A device as defined in claim 6, wherein said prosthesis models have a core composed of a material for reinforcing said synthetic plastic.

8. A device as defined in claim 1, wherein said applicator is composed of a bar having an end provided with a pincer-shaped receiving part for receiving prosthesis model.

9. A device as defined in claim 8, wherein said applicator is composed of a material selected from the group consisting of metal and synthetic plastic.

10. A device as defined claim 8, wherein said pincer-shaped receiving part is springy.

11. A device as defined in claim 8, wherein said pincer-shaped receiving part has an inner side which is routed.

12. A device as defined in claim 1, wherein individual parts of the device are packable in a package in sterile condition.

* * * * *